United States Patent [19]

Akiyama et al.

[11] 4,102,342
[45] Jul. 25, 1978

[54] VALVED DEVICE

[75] Inventors: Taichiro Akiyama, Tokyo; Sajiro Ookubo, Oomiya; Setsuko Ueno, Tokyo, all of Japan

[73] Assignee: Taichiro Akiyama, Tokyo, Japan

[21] Appl. No.: 752,076

[22] Filed: Dec. 20, 1976

[30] Foreign Application Priority Data

Dec. 29, 1975 [JP] Japan .................................. 50-156317
May 28, 1976 [JP] Japan .............................. 50-69345[U]

[51] Int. Cl.² ............................................. A61B 17/12
[52] U.S. Cl. .................................. 128/325; 128/342; 128/344; 128/349 BV; 251/342; 251/DIG. 2
[58] Field of Search .................... 128/276, 325, 349 B, 128/349 BV, 344, 351, 2 Z, 342; 251/342, DIG. 2

[56] References Cited

U.S. PATENT DOCUMENTS

| 2,493,326 | 1/1950 | Trinder | 128/325 |
| 2,566,806 | 9/1951 | Miller | 128/276 X |
| 2,647,515 | 8/1953 | Pollock et al. | 128/325 |
| 2,691,985 | 10/1954 | Newsom | 128/325 |
| 3,081,773 | 3/1963 | Isaac | 128/344 X |
| 3,375,828 | 4/1968 | Sheridan | 128/276 X |
| 3,407,817 | 10/1968 | Galleher, Jr. | 128/349 B UX |
| 3,903,893 | 9/1975 | Scheer | 128/325 |

FOREIGN PATENT DOCUMENTS

733,890  7/1955  United Kingdom .......... 128/349 BV

Primary Examiner—Robert W. Michell
Assistant Examiner—Michael H. Thaler
Attorney, Agent, or Firm—McDougall, Hersh & Scott

[57] ABSTRACT

A fluid such as air is tightly enclosed in a chamber which serves to plug an organic passage such as a person's nasal cavity. The fluid is supplied into the chamber through a tube so as elastically to expand the chamber and thereafter is discharged through a valve device comprising an opening formed in the tube and a valve member which normally closes the opening but can be rolled up on itself so that the fluid in the chamber can flow out through the opening.

8 Claims, 12 Drawing Figures

VALVED DEVICE

BACKGROUND OF THE INVENTION

1. Field of the Invention

This invention relates generally to a valve device. The valve device is particularly, but not exclusively, suitable for an instrument for preventing outflow of a nosebleed, or for a trachea cannula for supplying an anesthetic into the lung.

2. Description of the Prior Art

Figure 1:
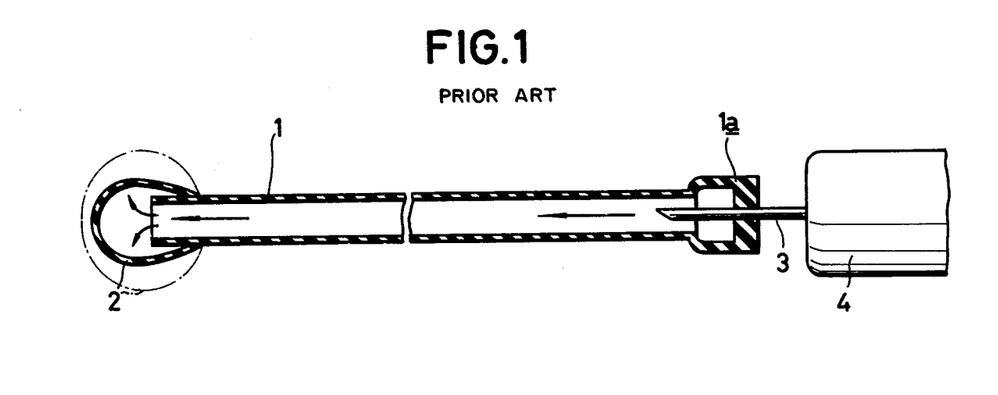
FIG. 1 is a cross-sectional view of a conventional instrument used for preventing outflow of a nosebleed.

The conventional instrument for preventing outflow of a nosebleed is shown in FIG. 1. The instrument comprises an elastic air accumulator or envelope 2 which is able to expand and contract and is attached to one end of a relatively rigid pipe 1 in such a manner that the envelope 2 encloses an open end of the pipe 1. The other end of the pipe 1 is formed with a relatively thick closed portion 1a of silicone rubber. To use the instrument, a needle 3 of an air injector 4 pierces the thick portion 1a as shown in FIG. 1 and the air is forcibly introduced into the pipe 1 with the injector 4. As a result, the air flows into the envelope 2 so that the envelope 2 is elastically expanded by the air pressure as shown by a dot-dash line. When the needle 3 is pulled out of the thick portion 1a, the pin hole formed by the needle 3 in the thick portion 1a closes by elastic restoration, and the air inside is trapped to maintain the envelope 2 expanded.

To use the instrument of FIG. 1 the envelope end is inserted into the nasal cavity. When the envelope 2 reaches the back nasal cavity, it is expanded by the air supplied through the needle 3 of the injector 4. As a result, the expanded envelope 2 tightly contacts a wall surface of the back nasal cavity so that blood entering the nasal cavity as a result of nosebleed cannot flow into the trachea through the back nasal cavity. This enables a nosebleed to be stanched, for example if a hemorrhage occurs during a surgical operation on the nasal cavity.

When the air in the envelope 2 is to be discharged, the needle 3 of the injector 4 is again pierced through the thick portion 1a, so that the air in the pipe 1 can be discharged by the injector 4, or alternatively the thick portion 1a is made as a cap which can be detached from the pipe 1. This is rather troublesome, as a separate instrument (the needle of the injector) or means (the cap) is required for discharging the air.

Again, in the conventional method for measuring an impedance in the middle ear, a detecting element (detecting probe) is inserted into a pipe which can be elastically deformed and is made of, for example, silicone rubber. The pipe with the detecting element is inserted into the concha passage. The pipe has a thick portion in which the detecting element is supported in the concha passage. However, the size of the concha passage varies from person to person, so the detecting element may slip out of the concha passage during the measurement of the impedance or alternatively the pipe may pass painfully on the concha passage.

SUMMARY OF THE INVENTION

Accordingly, an object of this invention is to provide a valve device which enables a fluid to be easily discharged without a separate discharging means.

Another object of this invention is to provide a valve device of simple construction.

A further object of this invention is to provide a valve device which can be attached to an instrument which can easily be inserted into an organic passage suitably to plug the latter, and then easily taken out from the organic passage.

A further object of this invention is to provide a valve device for an instrument used for preventing outflow of a nosebleed, or for a trachea cannula for supplying an anesthetic into the lung.

A still further object of this invention is to provide a valve device which is attached to an instrument with a detecting means to be suitably supported in an organic passage in order to measure an impedance therein.

In accordance with one aspect of the present invention there is provided a valve device for enabling a fluid enclosed in a chamber to be discharged, the device comprising: a first member having an interior portion which in use of the device communicates in fluid-tight manner with said chamber;

an opening in said first member which communicates said interior portion with the exterior of said first member; and a resilient valve member which normally closes said opening and which has an end portion from which said valve member can be rolled up on itself such that said opening is exposed to permit discharge of said fluid.

The above and other objects, features and advantages of this invention will become apparent from the following detailed description of illustrative embodiments shown in the accompanying drawings.

DESCRIPTION OF THE PREFERRED EMBODIMENTS

An instrument for preventing outflow of a nosebleed and including a valve device according to a first embodiment of the invention will be described with reference to FIGS. 2 to 7.

Figures 2, 3:
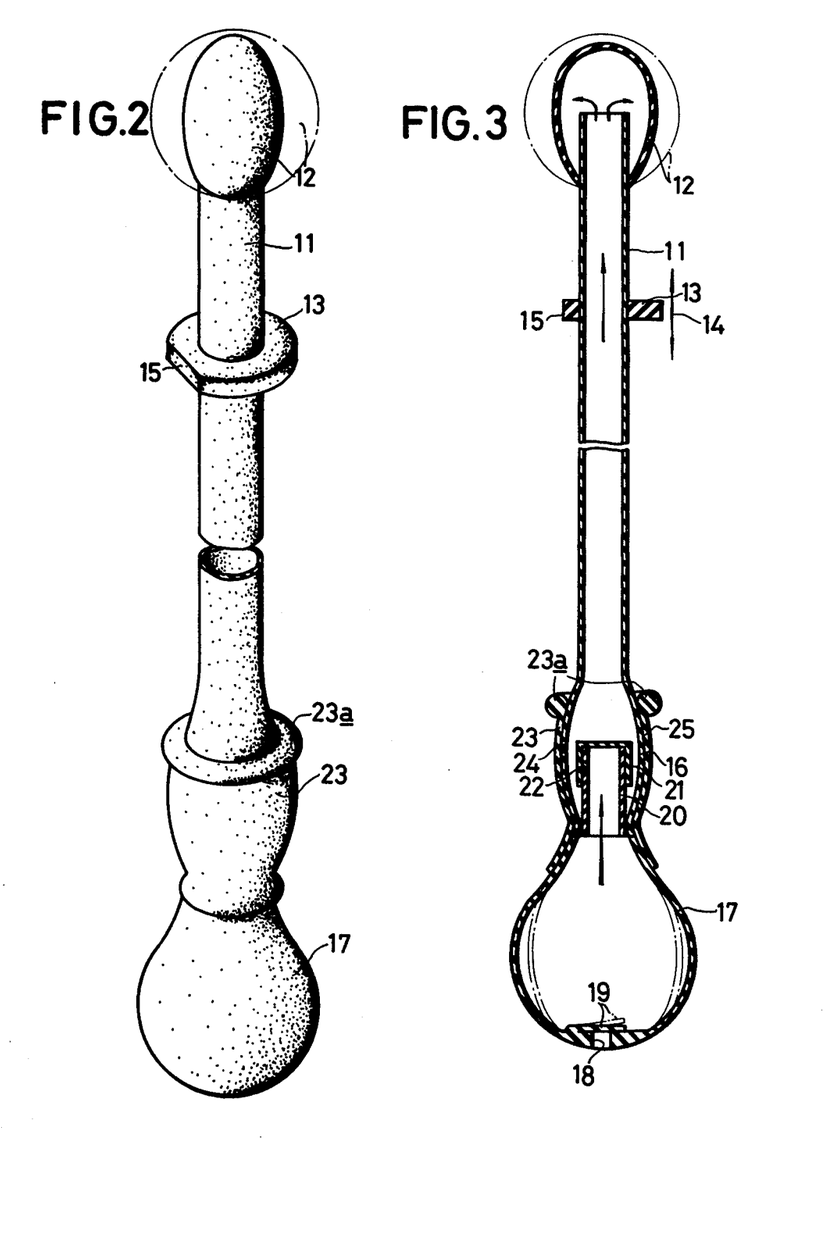
FIG. 2 is a perspective view of an instrument used for preventing outflow of a nosebleed and including a valve device according to a first embodiment of this invention.
FIG. 3 is a cross-sectional view of the instrument of FIG. 2.

Referring to FIGS. 2 and 3 an instrument is made of an elastomer (elastic high molecular compound) such as a silicone rubber, a natural or synthetic rubber or the like, and includes a pipe 11 with a wall thickness of about 0.5 mm and an external diameter of about 2.5 mm. An air accumulator or envelope 12 is fixed to one end of the pipe 11. The envelope 12 is elastic and can be expanded and contracted, that is to say, it can be expanded by internal air pressure from an external diameter of about 15 mm in a normal state to 45 to 50 mm, and then can be contracted by its elasticity to press out the air therefrom. A locating ring 13 used for determining the insertion depth of the pipe 11 into the nassal cavity can slide on the external surface of the pipe 11 in the longitudinal direction as indicated by an arrow 14, so that the position of the locating ring 13 can be freely adjusted. The locating ring 13 has an external diameter larger than the diameter of an inlet opening of the nasal cavity or nostrils and therefore if the position of the locating ring 13 is fixed after the insertion depth has been estimated, the pipe 11 cannot be inserted too far into the nasal cavity. The locating ring 13 has a flat surface 15 which contacts an external surface of the upper lip (FIG. 7) and serves to support the pipe 11 stably.

An enlarged cross-sectional portion 16 projecting outward to some extent is formed on the other end of the pipe 11. A bulb pump 17 for supplying air into the envelope 12 is fixed to the enlarged cross-sectional portion 16 in such a manner that said other end of the pipe 11 is closed. When the bulb pump 17 is compressed by the fingers, it is elastically deformed so that its volume is decreased as shown by a dot-dash line. The bulb pump 17 then elastically restores to the former shape to such external air thereinto through an air inlet opening 18 formed in a wall of the bulb pump 17. A sheet-like non-return valve member 19 closes the inlet opening 18 in the normal state and is formed on an internal surface of the bulb pump 17. One end of the valve member 19 is fixed to the internal surface and another part merely contacts the internal surface. An air suction force is developed when the bulb pump 17 elastically restores to the former shape, so that the valve member 19 is lifted up as shown by a dot-dash line and external air is sucked into the bulb pump 17 through the inlet opening 18.

One end of a small inner pipe 20 with a wall thickness of about 1 mm and an internal diameter of about 2 mm is fixed to the inside of the enlarged cross-sectional portion 16. Accordingly, the internal space in the pipe 20 communicates with the internal space in the bulb pump 17. A non-return valve member 21 with a thickness of 0.2 to 0.3 mm is fixed on the other end of the pipe 20 to close it. The valve member 21 is substantially cylindrical, with one end closed, and tightly contacts an external surface of the pipe 20 in the normal state. The pipe 20 has a few air inlet openings 22 with a diameter of about 0.8 mm which are normally closed by the valve member 21. When an air pressure is developed by the bulb pump 17, a small gap is opened between the valve member 21 and the pipe 20 against the elastic force of the valve member 21, which permits the air to flow into the pipe 11 from the pipe 20 through the opening 22 and said small gap.

A roller valve member 23 with a thickness of about 0.4 mm and a length of about 20 mm is tightly attached to an external surface of the enlarged cross-sectional portion 16 of the pipe 11. One end of the roller valve member 23 is fixed to the bulb pump 17 and another part of the valve member 23 merely elastically contacts the pipe 11.

Next, the operation of the instrument will be explained with reference to FIGS. 4 to 6.

Figure 4:
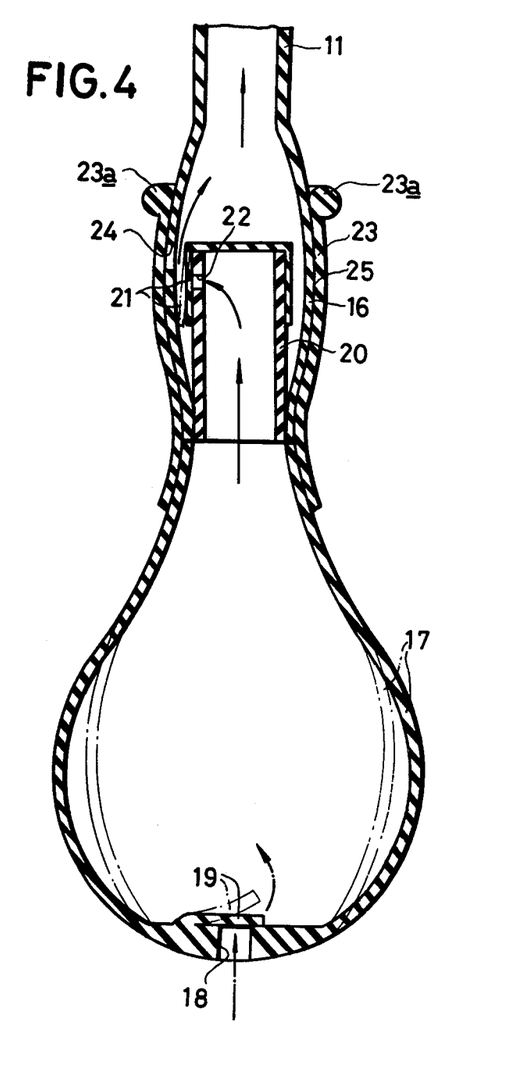
FIG. 4 is an enlarged cross-sectional view of a part of the instrument of FIG. 3.

As shown in FIG. 4, the bulb pump 17 is pressed from opposing sides by the fingers so that the bulb pump 17 is elastically contracted as shown by a dot-dash line. As a result, air is forced into the pipe 20 from the bulb pump 17 and escapes outward through the openings 22. In other words, air pressure developed in the pipe 20 functions to spread the valve member 21, so that the valve member 21 is elastically deformed as shown by the dot-dash line and the small gap is formed between the pipe 20 and the valve member 21. Air therefore enters the pipe 11. At first the air has not sufficient pressure to expand the envelope 12.

When the fingers release the bulb pump 17, the bulb pump 17 elastically restores to the former shape. External air then enters the bulb pump 17 through the opening 18, but the valve member 21 prevents air in the pipe 11 from flowing back into the pipe 20 through the opening 22. The valve member 19 lifts as shown by the dot-dash line in FIG. 4, so that external air flows into the bulb pump 17 through the opening 18 until the bulb pump 17 is completely restored to the former shape.

As a result, the bulb pump 17 again contains the same amount of internal air as at the beginning, that is to say, an amount of air corresponding to the amount of the air that flowed into the pipe 11 from the bulb pump 17 enters the bulb pump 17 from outside.

The alternate contraction and expansion of the bulb pump 17 is continued to expand the envelope 12 as shown by a dot-dash line in FIG. 3. When the envelope 12 has been expanded to the required extent, the valve element 21 is pressed against the pipe 20 by the action of the air pressure in the pipe 11 and therefore the air in the pipe 11 and the envelope 12 is retained in airtight manner.

The expanded envelope 12 is used to prevent the outflow of blood from nosebleed by tightly contacting a wall surface of the back nasal cavity as mentioned below.

When the pipe 11 with the envelope 12 is to be removed from the nasal cavity, it is necessary to contract the envelope 12. This is done using the roller valve member 23. An opening 24 for discharging the trapped air is formed in a side wall of the enlarged cross-sectional portion 16 of the pipe 11 and the roller valve member 23 normally tightly elastically contacts the pipe 11 so that the air cannot escape therefrom. By placing one or more fingers on a ring-shaped end 23a of the roller valve member 23, the roller valve member 23 can be forcibly rolled up on itself towards the enlarged cross-sectional portion 16 as shown by an arrow 26. The roller valve member 23 is thus rolled up to form a substantially spiral cross-section and a ring-shaped appearance with the end 23a of the roller valve member 23 located at the inside of the substantially spiral cross-section. The roller valve member 23 can very easily be rolled up as shown in FIG. 5 because it is thin and substantially cylindrically located around the external surface of the enlarged cross-sectional portion 16 in its original state. Moreover, the enlarged cross-sectional portion 16 has an inclined external surface 25 which becomes of smaller external diameter in the direction along which the roller valve member 23 is rolled up, and therefore the rolling-up operation can more easily be effected.

Figure 5:
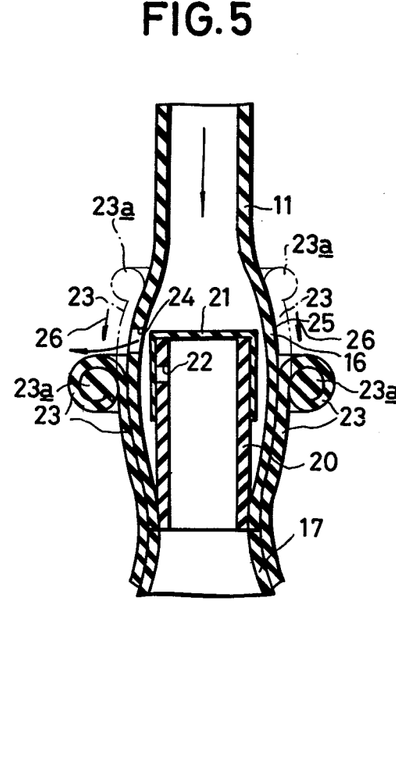
FIG. 5 is an enlarged cross-sectional view similar to FIG. 4 when a valve member is rolled up.
Figure 6:
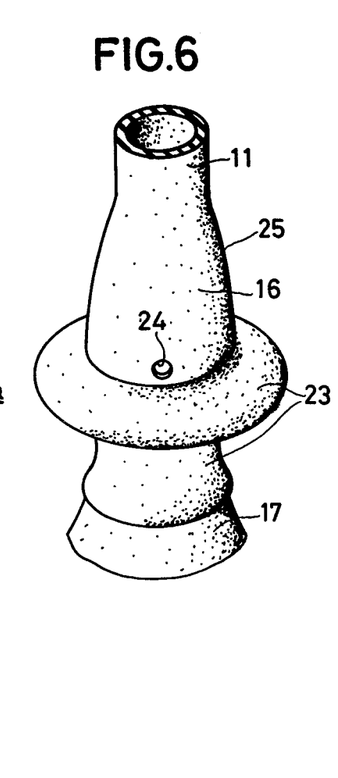
FIG. 6 is a perspective view of the instrument of FIG. 5.

When the condition shown in FIG. 5 and FIG. 6 is maintained, the opening 24 of the pipe 11 is exposed, so that the air previously trapped in the pipe 11 flows out rapidly through the opening 24. This continues until the envelope 12 is restored to the original collapsed size.

After the air in the pipe 11 has been discharged, the pressure by the finger on the roller valve member 23 which has maintained the spiral cross-section shown in FIG. 5 until that time is removed, so that the roller valve member 23 tends elastically to extend in the unrolling direction to be restored to the former configuration in which it tightly contacts the external surface of the pipe 11 and again completely closes the opening 24.

Discharging of the air can very easily be effected, and also the construction of the instrument can be simple because the roller valve member 23 is merely attached to the instrument.

Next, a practical method of using the instrument will be explained referring to FIG. 7.

First the end of the pipe 11 with the envelope 12 is inserted into the nasal cavity 27 from an inlet opening 28 thereof and subsequently introduced gradually towards the interior of the nasal cavity 27. At this time, if the position of the locating ring 13 is fixed after the insertion depth of the pipe 11 in the nasal cavity 27 being estimated, the envelope 12 will be located just at the back nasal cavity 29 when the locating ring 13 contacts the inlet opening 28. The pipe 11 is deformed to correspond to the shape of the nasal cavity 27, because it has good elasticity, and the flat surface 15 of the locating ring 13 contacts the external surface of the upper lip so that the pipe 11 is stably positioned after the insertion and moreover the insertion operation can be smoothly effected.

The envelope 12 is then expanded by the bulb pump 17 until it tightly contacts a wall surface of the back nasal cavity 29 so that this is plugged. As a result, blood from a nosebleed and entering the nasal cavity 27 can be prevented from flowing into the trachea 30 through the back nasal cavity 29. This permits a surgical operation on the nasal cavity to be more successfully effected. Moreover, when the instrument is to be taken out from the nasal cavity 27, the roller valve member 23 is rolled up so that the air in the pipe 11 is discharged therefrom. As a result, the volume of the envelope 12 is decreased and the pipe 11 can be easily taken out from the nasal cavity 27.

Figure 7:
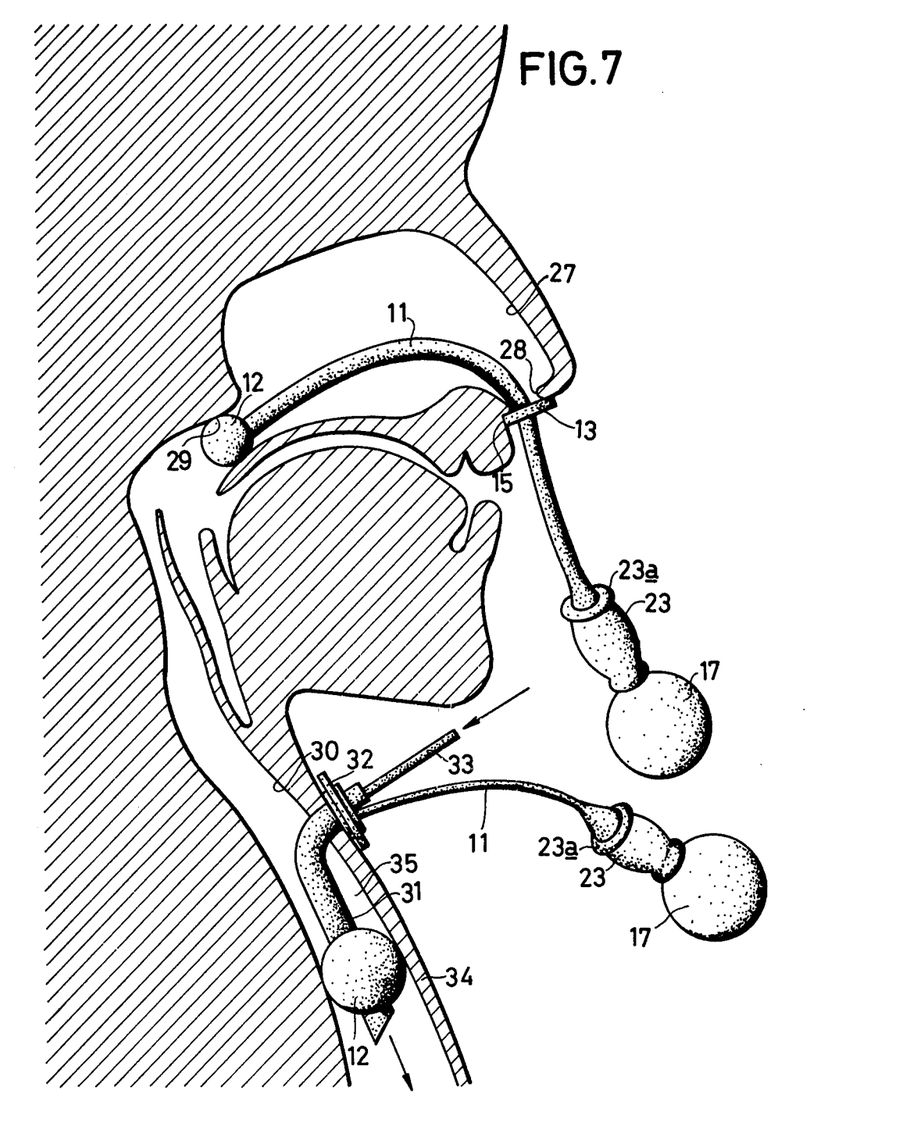
FIG. 7 is a cross-sectional view of the instrument inserted into an organic passage.
Figures 8, 9:
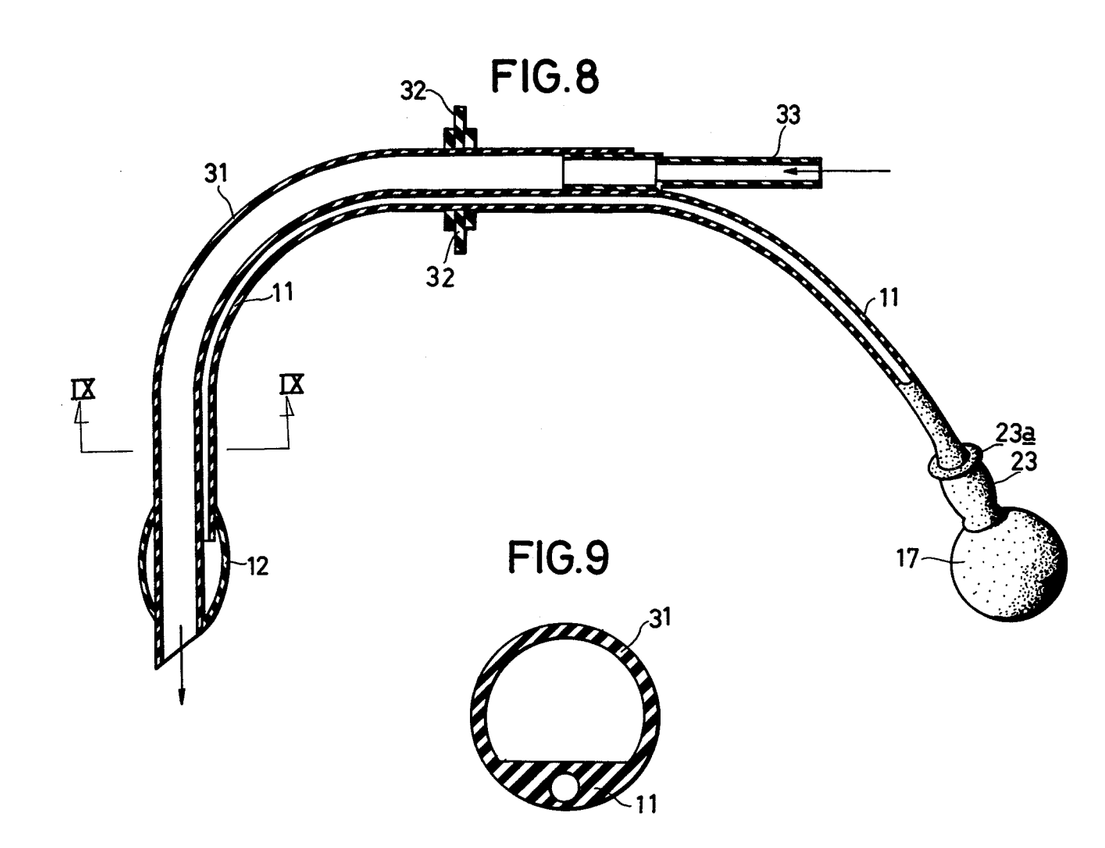
FIG. 8 is a cross-sectional view of a trachea cannula used for supplying an anesthetic into the lung and including a valve device according to a second embodiment of this invention.
FIG. 9 is a cross-sectional view taken along the line IX—IX in FIG. 8.

FIG. 7 to FIG. 9 show a second embodiment of the valve device applied to a trachea cannula for supplying an anesthetic into the lung.

The trachea cannula includes a pipe 31, one end of which is cut obliquely. Associated with the pipe 31 is an instrument generally as described above, and part of the length of the pipe 11 of the instrument is buried in the wall of the pipe 31. The envelope 12 is attached around an external surface of an end region of the pipe 31 adjacent to the oblique end. The pipe 11 is branched off from the other end of the pipe 31 and is connected to the bulb pump 17. The roller valve member 23 is attached to the enlarged cross-sectional portion 16 adjacent to the bulb pump 17.

A locating plate 32 for controlling the insertion depth of the cannula into the trachea is attached to the other end region of the pipe 31. A pipe 33 for supplying an anesthetic gas is inserted into this end of the pipe 31.

As shown in FIG. 7, the cannula is pierced into the neck 34 of a patient from the front and is inserted into the trachea 30 until the leading end of the cannula is directed towards the lung along the length of the trachea 30. In such a condition a gap 35 is formed between the pipe 31 and the wall surface of the trachea 30 and therefore the patient can breathe through the gap 35. When the patient takes a breath, the anesthetic gas is simultaneously sucked into the lung through the pipes 33 and 31.

When air is forcibly introduced into the envelope 12 through the pipe 11 by operation of the bulb pump 17, the envelope 12 is expanded tightly to contact the wall surface of the trachea 30. As a result, a counter flow of the supplied anesthetic gas can be effectively prevented, because the trachea 30 is instantaneously plugged by the expanded envelope 12.

Subsequently the roller valve member 23 is rolled up on itself as described above to discharge the air in the envelope 12, so that the trachea 30 is opened again, which permits the patient to breathe normally in such a manner that the anesthetic gas previously supplied to the lung acts upon the lung effectively.

Figure 10:
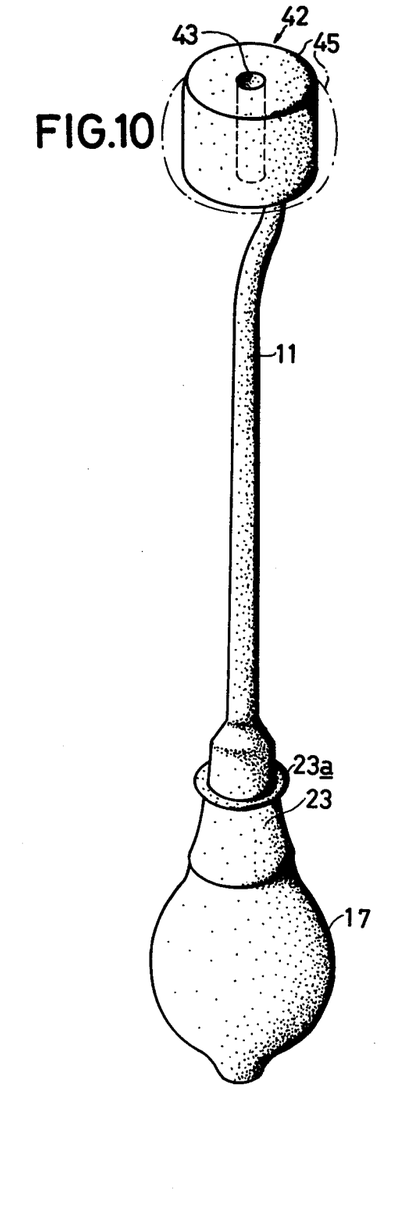
FIG. 10 is a perspective view of a supporting device for a detecting element used for measuring an impedance in the middle ear and including a valve device according to a third embodiment of this invention.
Figure 11:
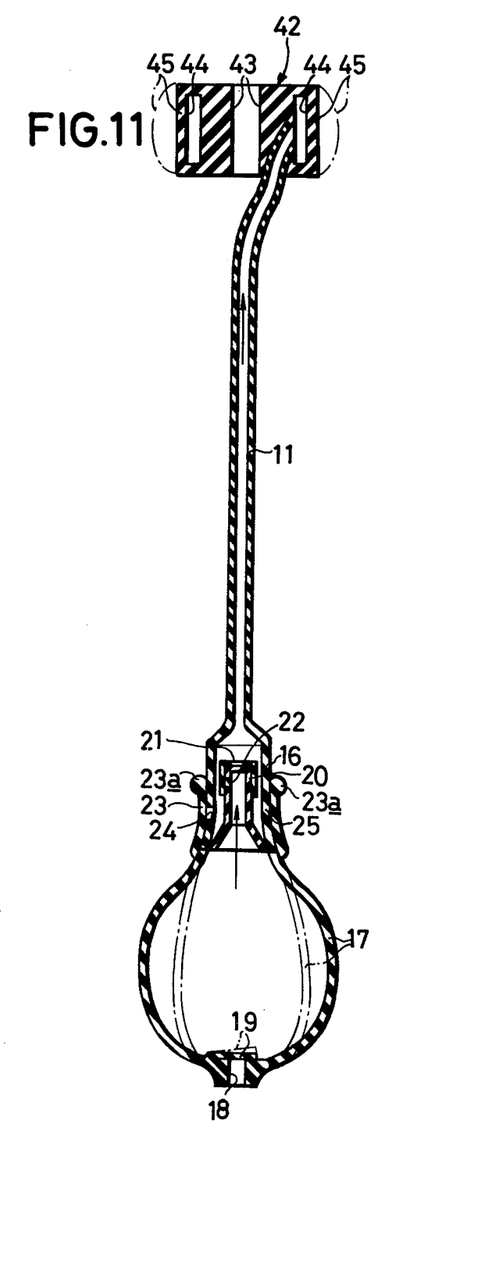
FIG. 11 is a cross-sectional view of the supporting device of FIG. 10.
Figure 12:
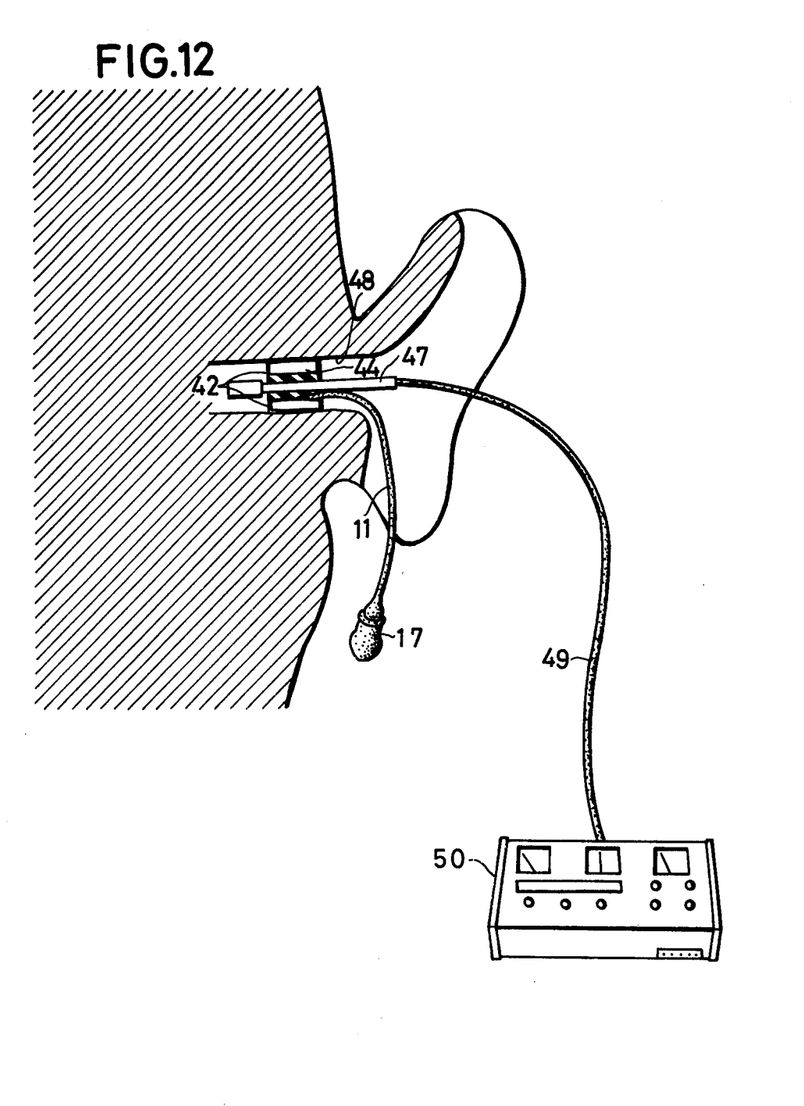
FIG. 12 is a cross-sectional view when the supporting device with the detecting element is inserted into the concha passage.

FIG. 10 to FIG. 12 show a third embodiment of valve device applied to a supporting device for a detecting element used for measuring an impedance in the middle ear.

A summary of the measurement of the impedance in the middle ear will first be given. In this measurement, the concha passage is tightly plugged and a sound pressure is applied from outside to generate a standing wave, so that the measurement of the impedance can be effected based upon a reflection coefficient of the standing wave reflected by the eardrum. With such a measurement the result is obtained in a much shorter time as compared with the usual measuring method of measuring and hearing for a pure tone. Moreover, the data obtained is objective because judgement by the patient is not necessary, so this method of measurement is increasingly used in the medical field.

During the measurement of the impedance in the middle ear, the detecting element must be supported stably within the tightly plugged concha passage.

Referring to FIGS. 10 and 11, an instrument for measuring the above impedance is made of an elastomer such as a silicone rubber, natural or synthetic rubber or the like and includes a pipe 11 with a wall thickness of about 0.5 mm and an external diameter of about 1.5 mm. A tube-like member 42 is fixed to one end of the pipe 11. A hole 43 with an internal diameter of about 2 mm for inserting a detecting element of an impedance measuring implement is formed through the center of the member 42. The external diameter of the detecting element is slightly larger than the internal diameter of the hole 43, for example, the former is 3 mm so that as the detecting element is inserted into the hole 43 the member 42 is elastically deformed and the detecting element is gripped in an airtight manner.

A ring-shaped chamber 44 for receiving air is formed around the external surface of the member 42. The chamber 44 communicates with the pipe 11 so that air can be supplied to the chamber 44. Air in the chamber 44 can be discharged through the pipe 11 by the action of the elastic force of a wall portion 45 defining an external surface of the chamber 44. The member 42 has an external diameter of, for example, 7 mm in the normal uniflated state, so that it can readily be inserted into the concha passage.

The same pump and valves as described in the first embodiment is attached to the other end of the pipe 11, and the same reference numerals are used in the drawings. In this embodiment, however, the enlarged cross-sectional portion 16 is substantially cylindrical, a part of the pipe 20 is circular truncated cone-shaped, and the length of the roller valve member 23 along the length of the enlarged cross-sectional portion 16 is about 5 mm.

Operation of the bulb pump 17 causes the chamber 44 to be expanded against the elastic force of the wall portion 45 as shown by a dot-dash line in FIGS. 10 and 11. The member 42 with the expanded chamber 44 tightly contacts the wall surface of the concha passage and serves to support the detecting element stably. To remove the member 44 from the concha passage, the roller valve member 23 is rolled up on itself along the enlarged cross-sectional portion 16 as shown in FIGS. 5 and 6. The air in the expanded chamber 44 is thus discharged through the opening 24 and the chamber 44 is elastically restored to the former state. The rolled up roller valve member 23 is also elastically restored to the former state by the action of its elastic force along the enlarged cross-sectional portion 16.

Next, the use of this instrument will be explained with reference to FIG. 12.

First, a detecting element 47 is inserted into the hole 43 of the member 42. The member 42 with the detecting element 47 is then inserted into the concha passage 48 of a patient. At this time air is not supplied to the chamber 44 through the pipe 11, so the external diameter of the member 42 is smaller than the internal diameter of the concha passage 48. Accordingly, the member 42 can readily be inserted into the concha passage 48 without pain to the patient.

When the member 42 has been inserted a predetermined depth into the concha passage 48, air is gradually introduced into the chamber 44 through the pipe 11 by operating the bulb pump 17. As a result, the chamber 44 is gradually expanded to enlarge the external diameter of the member 42 and the external surface of the member 42 elastically and tightly contacts the wall surface of the concha passage 48.

Consequently, the member 42 is stably supported in the concha passage 48 and also the detecting element 47 is stably supported substantially in the center of the cross-section of the concha passage 48. In this condition, the detecting element 47 does not contact the wall surface of the concha passage 48 and the measurement of the impedance can be accurately effected. Moreover, even if the cross-section of the concha passage 48 is not substantially circular, the detecting element 47 can be supported stably because the chamber 44 elastically conforms to the shape of the concha passage 48 when it is expanded.

A lead 49 is connected to the detecting element 47 and an output signal from the detecting element 47 is supplied to an impedance meter 50 through the lead 49. Accordingly, a numerical value indicated by a needle of the impedance meter 50 is directly read or the numerical value is recorded by an XY-recorder (not shown), so that the measurement of the impedance in the middle ear can be effected.

When the measurement has been done, the roller valve member 23 is rolled up as shown in FIGS. 5 and 6 to discharge the air in the chamber 44 through the opening 24 of the enlarged cross-sectional portion 16. As a result, the external diameter of the member 42 becomes smaller, so that the member 42 can easily be taken out from the concha passage 48.

While preferred embodiments of this invention have been described using specific terms, such descriptions are for illustrative purposes only, and it is to be understood that changes and variations may be made without departing from the spirit and scope of the following claims.

For example, in the first and second embodiments, the roller valve member 23 can be directly attached to a part of the enlarged cross-sectional portion 16 of the pipe 11 or can be attached to the bulb pump 17 and the enlarged cross-sectional portion 16. The enlarged cross-sectional portion 16 may not necessarily be provided. The shapes of the roller valve member 23 and the pipe 11 can be also variously changed. Instead of as in the above-mentioned preferred embodiments, the roller valve member 23 can be attached to the conventional instrument shown in FIG. 1 wherein the air is forcibly introduced into the pipe 1 with the injector and the air in the envelope 2 is discharged by the use of the roller valve member 23. Although air is forcibly introduced into the pipe 11 in the preferred embodiments, any other fluid which is able easily to expand the envelope 12 can be used. In FIG. 7 the pipe 33 can be further extended so that the air can be sucked into the trachea 30 through the extended pipe 33. On this occasion, when the patient is taking a bath, an upper end of the extended pipe 33 is located above the level of hot water and the envelope 12 is expanded with the bulb pump 17 to tightly contact the wall surface of the trachea 30, whereby the patient can breathe through the extended pipe 33. Moreover, this invention can be applied to any instruments used for plugging or opening a hole or for measuring an impedance in any organic passage of a living body.

What is claimed is:

1. A valved device including a chamber, an outer pipe having an interior portion which normally communicates in fluid-tight manner with the interior of said chamber, an opening being provided in said outer pipe and communicating said interior portion with the exterior of said outer pipe, and a hollow valve member attached in surrounding relationship with said outer pipe in such a manner that said opening is normally closed by said valve member, said valve member being adapted to be rolled up on itself along said outer pipe into a ring-shaped configuration whereby said opening is exposed to permit discharge of said fluid, said valve member being attached to a tapered surface of said outer pipe, the valve member being formed of an elastic material with sufficient elasticity such that the valve member normally resists being rolled up on itself and is elastically restored by its elastic force to its original state to close said opening when rolling force is removed, said chamber comprising an envelope connected to said outer pipe, said envelope being adapted to elastically expand and contract, and wherein said envelope is adapted to be expanded by forcibly supplying a fluid through said pipe, and said envelope contracts by the action of its elastic force so that a fluid in said envelope is discharged through said pipe and said exposed opening when said valve member is rolled up.

2. A valve device according to claim 1, in which a means for supplying said fluid into said chamber is attached to said pipe.

3. A valve device according to claim 2, in which said fluid is air and said means for supplying said air is a bulb pump, and a non-return valve associated with said bulb pump; said bulb pump being adapted to be repeatedly expanded and contracted to force air from said bulb pump into said pipe through said non-return valve to expand said chamber.

4. A valve device according to claim 3, comprising an inner pipe, with a hole in the wall of said inner pipe said non-return valve comprising a cylindrical member attached to said inner pipe and fixed to an outer surface of said inner pipe adjacent said hole, whereby said cylindrical member covers said hole, said non-return valve being forcibly opened by the air pressure resulting from said bulb pump being contracted and being closed by its own elastic force, and another non-return valve being provided in a wall of said bulb pump to enable external air to be sucked into said bulb pump.

5. A valve device according to claim 1, in which said envelope is insertable into a nasal cavity together with said pipe and can then be expanded tightly to contact a wall surface of said nasal cavity, whereby said nasal cavity is plugged and outflow of a nosebleed can be prevented.

6. A valve device according to claim 1, in which said envelope is attached to an end of a trachea cannula to enable gas to be supplied into the lung and said pipe is attached along said trachea cannula, said envelope being expandable to plug the trachea to prevent a counterflow of said gas.

7. A valve device according to claim 1, in which said envelope is formed around a supporting device for an element for detecting an impedance in an organic passage of a living body, said element being inserted into an aperture formed at the center of said supporting device.

8. A valve device according to claim 7, in which said supporting device with said element is insertable into the ear passage and said envelope is expandable tightly to contact a wall surface of said ear passage so as to plug said ear passage and to support said element therein.

* * * * *